United States Patent
Kudlik et al.

(10) Patent No.: US 11,694,539 B2
(45) Date of Patent: Jul. 4, 2023

(54) NOTIFICATION SYSTEM FOR LOW-LEVEL PREVENTATIVE LVAD ALERTS

(71) Applicant: HeartWare, Inc., Miami Lakes, FL (US)

(72) Inventors: D'Anne E. Kudlik, Saint Louis Park, MN (US); Joseph Ippolito, Shoreview, MN (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 17/192,028

(22) Filed: Mar. 4, 2021

(65) Prior Publication Data

US 2021/0390841 A1 Dec. 16, 2021

Related U.S. Application Data

(60) Provisional application No. 63/039,596, filed on Jun. 16, 2020.

(51) Int. Cl.
| | |
|---|---|
| *G08B 21/02* | (2006.01) |
| *G08B 21/24* | (2006.01) |
| *G08B 7/06* | (2006.01) |
| *A61M 60/508* | (2021.01) |
| *A61M 60/17* | (2021.01) |

(52) U.S. Cl.
CPC ............ *G08B 21/24* (2013.01); *A61M 60/17* (2021.01); *A61M 60/508* (2021.01); *G08B 7/06* (2013.01); *A61M 2205/18* (2013.01); *A61M 2205/581* (2013.01); *A61M 2205/582* (2013.01); *A61M 2205/583* (2013.01)

(58) Field of Classification Search
USPC ............. 340/539.11, 573.1, 539.12, 539.22, 340/539.26, 568.8, 683, 692
See application file for complete search history.

(56) References Cited

U.S. PATENT DOCUMENTS

| | | | |
|---|---|---|---|
| 6,268,161 B1* | 7/2001 | Han | A61B 5/0031 436/95 |
| 7,997,854 B2 | 8/2011 | LaRose et al. | |
| 8,007,254 B2 | 8/2011 | LaRose et al. | |
| 8,419,609 B2 | 4/2013 | Shambaugh, Jr. et al. | |
| 8,512,013 B2 | 8/2013 | LaRose et al. | |
| 9,561,313 B2 | 2/2017 | Taskin | |
| 10,130,743 B2 | 11/2018 | Yeatts | |
| 2008/0195061 A1* | 8/2008 | Fobi | G16H 50/20 604/246 |
| 2010/0184742 A1* | 7/2010 | Uhr | C12Q 1/6883 435/6.12 |
| 2011/0032107 A1* | 2/2011 | Sasaki | A61M 60/50 600/300 |
| 2017/0182232 A1* | 6/2017 | Rudser | G05B 17/02 |
| 2017/0372592 A1* | 12/2017 | Neravati | G08B 21/0446 |

(Continued)

OTHER PUBLICATIONS

International Search Report and Written Opinion dated Sep. 1, 2021, for corresponding International Application No. PCT/US2021/034395; International Filing Date: May 27, 2021 consisting of 10-pages.

*Primary Examiner* — Daniel Previl
(74) *Attorney, Agent, or Firm* — Shumaker & Sieffert, P.A.

(57) ABSTRACT

A controller for an implantable blood pump including processing circuitry in communication with the implantable blood pump and configured to generate at least one preventative alert.

20 Claims, 3 Drawing Sheets

(56) References Cited

U.S. PATENT DOCUMENTS

| | | | |
|---|---|---|---|
| 2019/0015040 A1* | 1/2019 | Voskoboynikov ... | A61B 5/7278 |
| 2019/0015571 A1* | 1/2019 | Voskoboynikov .. | A61M 60/148 |
| 2019/0111197 A1 | 4/2019 | Yeatts | |
| 2019/0189274 A1* | 6/2019 | Kalia ................. | H04L 63/0876 |
| 2019/0255235 A1* | 8/2019 | Sambelashvili ...... | A61M 5/172 |
| 2019/0255237 A1 | 8/2019 | Cinbis | |
| 2019/0351116 A1* | 11/2019 | Kudlik ................ | A61M 60/546 |
| 2020/0129099 A1* | 4/2020 | Mi ..................... | A61B 5/02405 |

\* cited by examiner

NOTIFICATION SYSTEM FOR LOW-LEVEL PREVENTATIVE LVAD ALERTS

CROSS-REFERENCE TO RELATED APPLICATION

This application claims the benefit of U.S. Application Ser. No. 63/039,596, filed Jun. 16, 2020.

FIELD

The present technology is generally related to preventative alerts for patients with implantable blood pumps.

BACKGROUND

Patients with implantable blood pumps typically have controllers that generate alarms when there is a problem with the pump or its operation. For example, during a suction or low flow event, a loud alarm will sound that alerts the user to the condition so that the user can visit a clinician for remediation. Such alarms are loud and very disruptive and the user and can only be silenced for a few minutes, which can disrupt a user's sleep. Moreover, such alarms are all reactive in nature. That is, the alarms are responsive to adverse events that have occurred.

SUMMARY

The techniques of this disclosure generally relate to preventative alerts for patients with implantable blood pumps.

In one aspect, the present disclosure provides a controller for an implantable blood pump including processing circuitry in communication with the implantable blood pump and configured to generate at least one preventative alert.

In another aspect of this embodiment, the at least one preventative alert includes an alert notifying a user to hydrate.

In another aspect of this embodiment, the at least one preventative alert includes an alert notifying a user to take medication.

In another aspect of this embodiment, the at least one preventative alert is a silent alert.

In another aspect of this embodiment, the at least one preventative alert is a vibratory alert.

In another aspect of this embodiment, the at least one preventative alert is an audible alert.

In another aspect of this embodiment, the at least one preventative alert is a text alert.

In another aspect of this embodiment, the at least one preventative alert is dismissible.

In another aspect of this embodiment, the processing circuitry is further configured to log the generated at least one preventative alert and to not generate a notification of the at least one preventative alert.

In one aspect, a method of operating a notification system of a controller for an implantable blood pump generating at least one preventative alert from the controller.

In another aspect of this embodiment, the at least one preventative alert includes an alert notifying a user to hydrate.

In another aspect of this embodiment, the at least one preventative alert includes an alert notifying a user to take medication.

In another aspect of this embodiment, the at least one preventative alert is a silent alert.

In another aspect of this embodiment, the at least one preventative alert is a vibratory alert.

In another aspect of this embodiment, the at least one preventative alert is an audible alert.

In another aspect of this embodiment, the at least one preventative alert is a text alert.

In another aspect of this embodiment, the at least one preventative alert is dismissible.

In one aspect, a controller for an implantable blood pump, the controller having a display, the controller a haptic device coupled to the controller and processing circuitry in communication with the implantable blood pump and with the haptic device, the processing circuitry being configured to generate at least one preventative alert as a vibratory alert from the haptic device and as a text alert on the display.

In another aspect of this embodiment, the at least one preventative alert is dismissible.

In another aspect of this embodiment, the at least one preventative alert is at least one from the group consisting of an alert notifying a user to hydrate and take medication.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
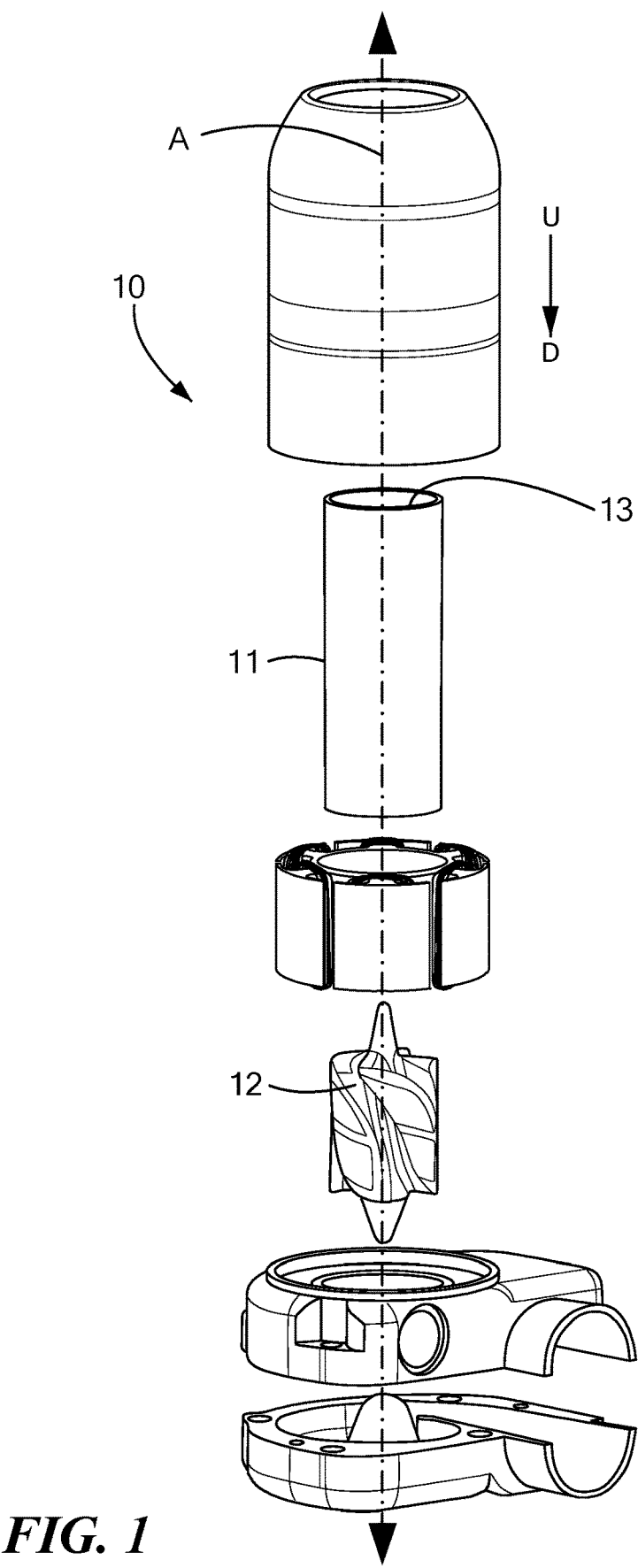
FIG. 1 is a disassembled view of an exemplary blood pump constructed in accordance with the principles of the present application.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® pump or the MVAD® pump, having a movable element, such as an impeller 12 or a rotor, configured to rotate about axis "A" and impel blood from the heart to the rest of the body. The impeller 12 may rotate within a tube 11 extending from a proximal upstream end to a distal downstream end. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
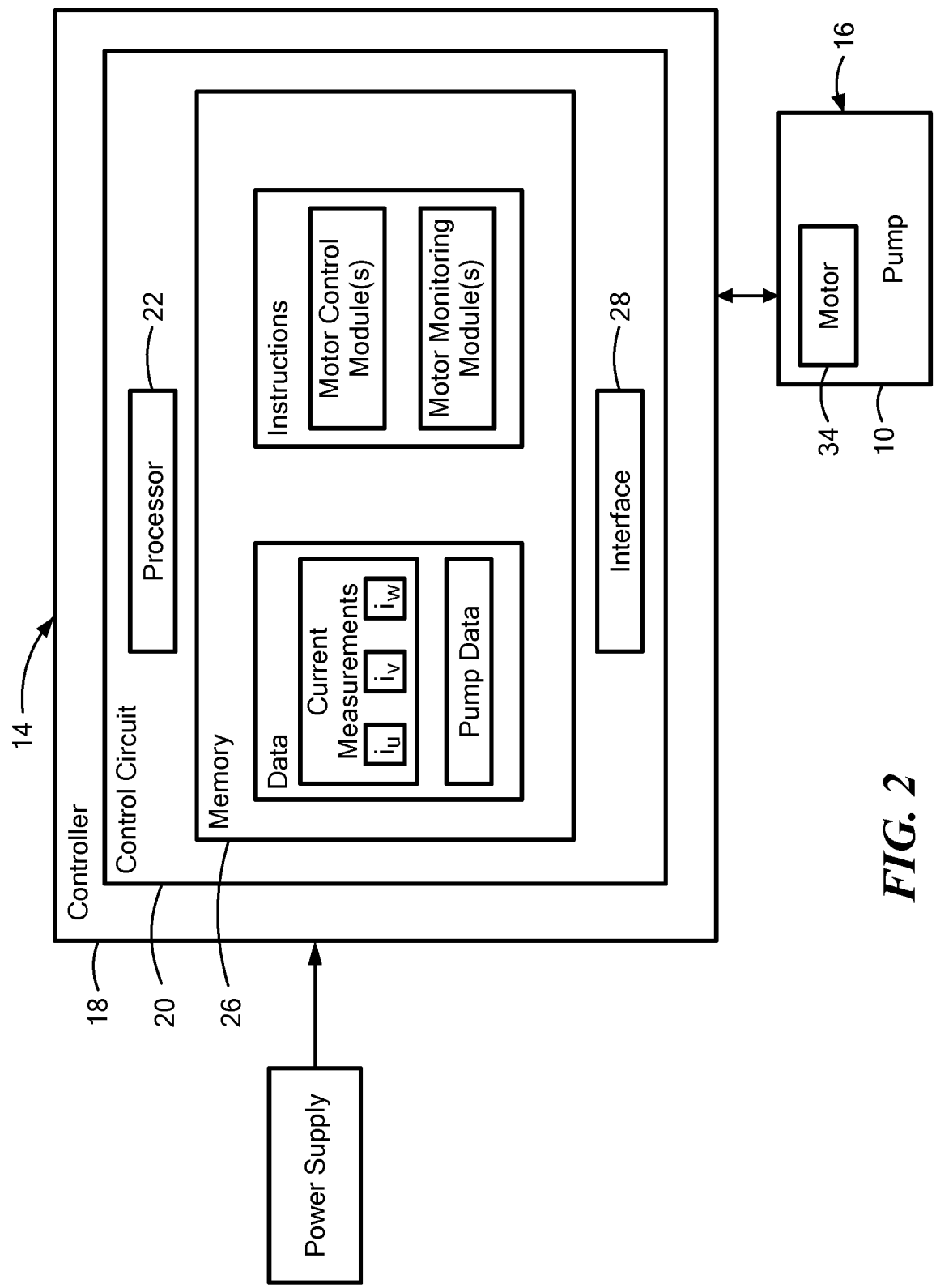
FIG. 2 is a block diagram showing a control system and pump of the present application.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed.

Figure 3:
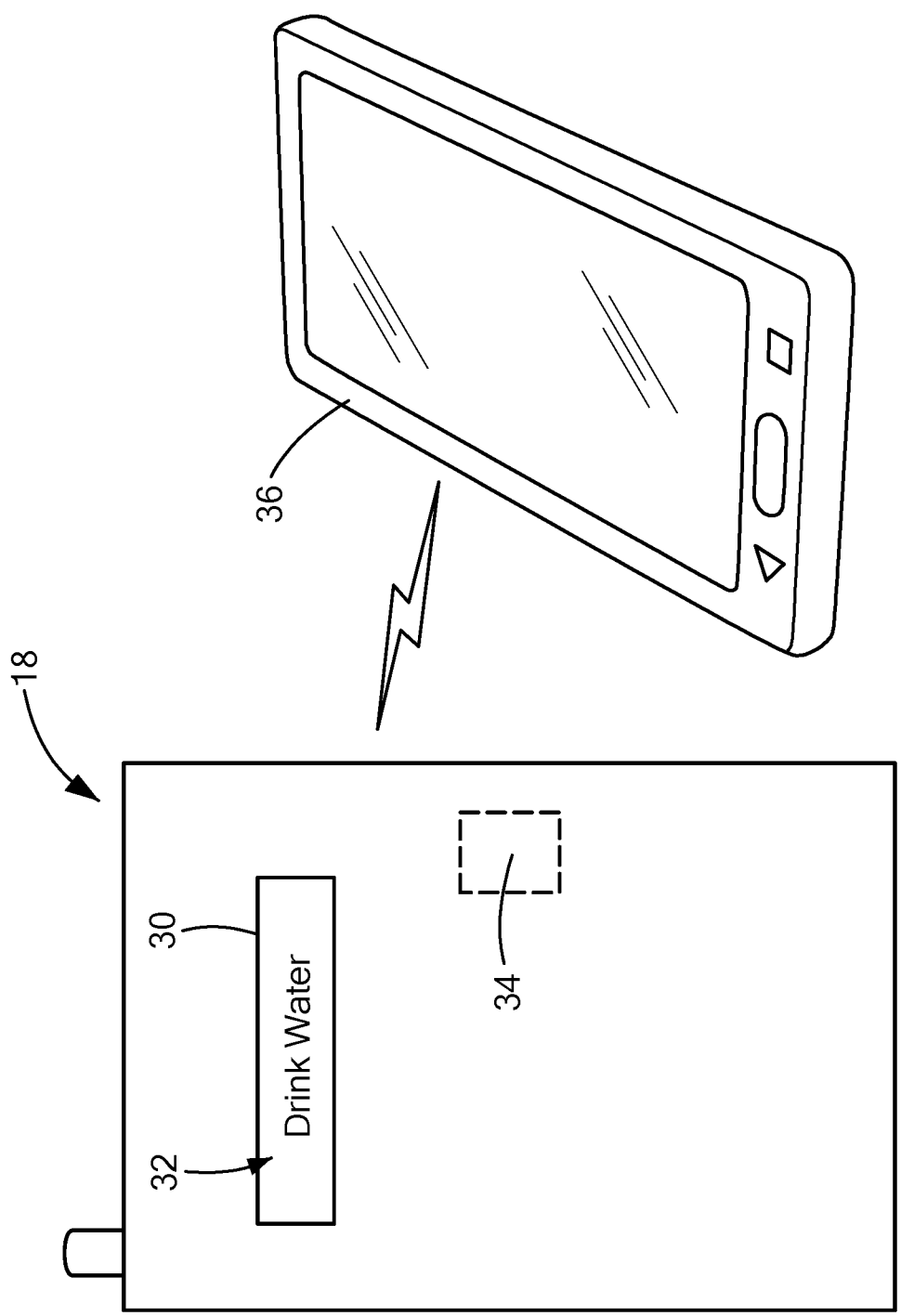
FIG. 3 is a front view of a controller constructed in accordance with the principles of the present application in communication with a Smartphone.

Referring now to FIG. 3, the controller 18, which is external to the patient, may include a display 30 configured to display at least one preventative alert 32 or optionally may include a haptic device 34 configured to vibrate to signal the at least one preventative alert 32. As used herein, preventative alerts refer to alerts that notify the user of pump to be proactive before an adverse event occurs. For example, such preventative alerts 32 include, but are not limited to an alert to notify the patient to hydrate or take medication, such as a blood thinner or blood pressure medication. In another words, preventative alerts 32 are configured to call the user to action to prevent a reactive alert, such as a suction alert. The preventative alerts 32 can be presented in any number of manners. For example, the preventative alert 32 may be displayed on the display 32 in the form of a push notification, for example, a text that reads "hydrate" or "drink water." In other configurations, the preventative alert 32 may cause the haptic device 34 or other circuitry within the controller to vibrate alone or in combination with the text alert. In another configuration, an audible alert may be generated, for example, a beep or other sound to notify the patient of the preventative alert 32. For example, sound generated by the controller 18 may correlated to a specific notification—a beep could mean to hydrate and a bell sound could mean to take medication. These features can be customizable by the user or the clinician. In other configurations, the preventative alert 32 may be a silent alert, for example, a message displayed on the display 30 of the controller 18. The preventative alerts 32 can be periodic, for example, every few hours as a reminder to drink water or on a set schedule that corresponds with a time to take medication. The preventative alerts 32 could also be generated is response to a detection algorithm, for example, suction detection. In particular, if suction is detected, the preventative alerts can be generated to call the user to perform an action, such as drink water. In one configuration, the preventative alerts 32 are dismissible by the user. For example, reactive alerts, such as suction alerts typically cannot be dismissed by the user or are preset to last for a longer duration of time, for example, over 5 minutes. In contrast, the user can instantly dismiss the preventative alerts 32 by pressing on an actuator (not shown) coupled to the controller 18 in communication with the processing circuitry 24. In other configurations, the controller 18 is configured to not generate an alert notifying the user of a preventative alert 32, but rather to log the alert in a database that can be retrieved by the clinician. For example, certain preventative alerts 32 may be turned off by the user or clinician, but may be logged by the controller 18 for future retrieval. For example, when a user is sleeping, and does not want to be disturbed, the preventative alerts 32 may be turned off or delayed during that period of time.

In another configuration, the controller 18 is configured to be in communication with a remote communications device 36, for example a Smartphone. For example, the controller 18 may pair with the remote communications device 36 via Bluetooth, or other similar connection such that the preventative alerts 32 may also be displayed by the remote communications device 36 either consecutively or substantially simultaneously when the preventative alert 32 is generated by the controller 18. In other configurations, the preventative alert 32 may only be displayed by the remote communications device 36. For example, when a user is in a public setting and may not want to check the controller 18, the use may optionally set the controller 18 such that preventative alerts 32 are only displayed by the remote communications device 36.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable blood pump, the controller comprising:
    processing circuitry in communication with the implantable blood pump and configured to:
        determine to generate at least one preventative alert before an adverse event occurs at the implantable blood pump based on a user input or a clinician input, wherein the at least one preventative alert is dismissible by a user; and
        generate at least one reactive alert in response to the adverse event occurring at the implantable blood pump, wherein the at least one reactive alert lasts for a longer duration of time than the preventive alert.

2. The controller of claim 1, wherein the at least one preventative alert includes an alert notifying the user to hydrate.

3. The controller of claim 1, wherein the at least one preventative alert includes an alert notifying the user to take medication.

4. The controller of claim 1, wherein the at least one preventative alert is an audible alert.

5. The controller of claim 1, wherein the at least one preventative alert is a vibratory alert.

6. The controller of claim 1, wherein the at least one preventative alert is a text alert.

7. The controller of claim 1, wherein the at least one reactive alert cannot be dismissed by the user for a predetermined duration of time.

8. The controller of claim 7, wherein the predetermined duration of time is five minutes.

9. The controller of claim 1, wherein the processing circuitry is further configured to log the at least one preventative alert and to not generate a notification of the at least one preventative alert.

10. The controller of claim 1, wherein the adverse event is a suction event.

11. The controller of claim 1, wherein the processing circuitry is further configured to:
when the user is sleeping,
log the at least one preventative alert; and
not generate a notification of the at least one preventative alert.

12. A method of operating a notification system of a controller for an implantable blood pump, the method comprising:
determining to generate at least one preventative alert from the controller before an adverse event occurs at the implantable blood pump based on a user input or a clinician input, wherein the at least one preventative alert is dismissible by a user; and
generating at least one reactive alert in response to the adverse event occurring, wherein the at least one reactive alert lasts for a longer duration of time than the preventive alert.

13. The method of claim 12, wherein the at least one preventative alert includes an alert notifying the user to hydrate.

14. The method of claim 12, wherein the at least one preventative alert includes an alert notifying the user to take medication.

15. The method of claim 12, wherein the at least one reactive alert cannot be dismissed by the user for a predetermined duration of time.

16. The method of claim 12, further comprising:
logging the at least one preventative alert; and
not generating a notification of the at least one preventative alert.

17. The method of claim 16, further comprising:
when the user is sleeping,
logging the at least one preventative alert; and
not generating a notification of the at least one preventative alert.

18. A controller for an implantable blood pump, the controller having a display, the controller comprising:
a haptic device coupled to the controller; and
processing circuitry in communication with the implantable blood pump and with the haptic device, the processing circuitry being configured to:
determine to generate at least one preventative alert as a vibratory alert from the haptic device and as a text alert on the display before an adverse event occurs at the implantable blood pump based on a user input or a clinician input, wherein the at least one preventative alert is dismissible by a user; and
generating at least one reactive alert in response to the adverse event occurring, wherein the at least one reactive alert lasts for a longer duration of time than the preventive alert.

19. The controller of claim 18, wherein the at least one reactive alert cannot be dismissed by the user for a predetermined duration of time.

20. The controller of claim 19, wherein the at least one preventative alert is at least one from the group consisting of an alert notifying a user to hydrate and take medication.

* * * * *